US010362782B2

(12) United States Patent
Oliveira et al.

(10) Patent No.: US 10,362,782 B2
(45) Date of Patent: *Jul. 30, 2019

(54) METHOD FOR CONTROLLING RUST

(71) Applicant: UPL LIMITED, Haldia, West Bengal (IN)

(72) Inventors: Gilson Aparecido Hermenegildo de Oliveira, Sao Paulo (BR); Jaidev Rajnikant Shroff, Maharashtra (IN); Vikram Rajnikant Shroff, Maharashtra (IN)

(73) Assignee: UPL Limited, Haldia, West Bengal (IN)

( * ) Notice: Subject to any disclaimer, the term of this patent is extended or adjusted under 35 U.S.C. 154(b) by 0 days.

This patent is subject to a terminal disclaimer.

(21) Appl. No.: 15/673,313

(22) Filed: Aug. 9, 2017

(65) Prior Publication Data
US 2017/0332637 A1    Nov. 23, 2017

Related U.S. Application Data

(63) Continuation of application No. 15/039,463, filed as application No. PCT/IB2014/064891 on Sep. 27, 2014, now Pat. No. 9,788,544.

(30) Foreign Application Priority Data

Nov. 26, 2013 (IN) .......................... 1336/KOL/2013

(51) Int. Cl.
| *A01N 55/02* | (2006.01) |
| *A01N 43/653* | (2006.01) |
| *A01N 43/54* | (2006.01) |
| *A01N 25/00* | (2006.01) |
| *A01N 47/14* | (2006.01) |
| *A01N 43/40* | (2006.01) |
| *A01N 47/24* | (2006.01) |

(52) U.S. Cl.
CPC ............. *A01N 43/54* (2013.01); *A01N 25/00* (2013.01); *A01N 43/40* (2013.01); *A01N 43/653* (2013.01); *A01N 47/14* (2013.01); *A01N 47/24* (2013.01)

(58) Field of Classification Search
CPC ............. A61K 31/4196; A61K 31/555; A61K 31/505; A61K 31/415; A61K 31/465
USPC ........ 514/384, 184, 269, 403, 355; 504/189, 504/190, 273
See application file for complete search history.

(56) References Cited

U.S. PATENT DOCUMENTS

| 9,788,544 | B2 * | 10/2017 | Oliveira | ................. | A01N 47/14 |
| 2002/0173529 | A1 * | 11/2002 | Dutzmann | ........... | A01N 43/653 |
| | | | | | 514/383 |
| 2012/0088665 | A1 * | 4/2012 | Dietz | ..................... | A01N 37/50 |
| | | | | | 504/100 |

FOREIGN PATENT DOCUMENTS

| CA | 2862939 A1 | 5/2005 |
| CN | 102273475 A | 12/2011 |
| CN | 103843800 A | 6/2014 |
| WO | 2008/095913 A2 | 8/2008 |
| WO | 2010/046927 A2 | 4/2010 |
| WO | 2010/132169 A1 | 11/2010 |
| WO | 2011/151261 A2 | 12/2011 |
| WO | 2012/117572 A1 | 9/2012 |

OTHER PUBLICATIONS

International Search Report and Written Opinion from corresponding International Patent Application No. PCT/IB2014/064891, dated Feb. 23, 2015, 20 pages.

* cited by examiner

*Primary Examiner* — Shengjun Wang
(74) *Attorney, Agent, or Firm* — IP Pundit LLC

(57) ABSTRACT

A combination comprising a multi-site contact fungicide, a first systemic fungicide and optionally a second systemic fungicide and a method using the same.

12 Claims, No Drawings

METHOD FOR CONTROLLING RUST

CROSS REFERENCE TO RELATED APPLICATIONS

This application is a Continuation Application of U.S. patent application Ser. No. 15/039,463, filed on May 26, 2016, which is a national phase application under 35 U.S.C. § 371 of International Application No. PCT/IB2014/064891, filed on Sep. 27, 2014, which claims priority to Indian Patent Application No. 1336/KOL/2013, filed on Nov. 26, 2013; the disclosures of all of which are hereby incorporated by reference in their entirety.

TECHNICAL FIELD OF THE INVENTION

The present invention relates to a method for the prevention and/or treatment of phytopathogenic fungi. More particularly, the present invention relates to a method of using fungicides for the prevention and/or treatment of Asian soybean rust in leguminous plants.

BACKGROUND OF THE INVENTION

The fungus of the genus *Phakopsora* is known to infect legumes. Two most prominent strains of the genus are *Phakopsora pachyrhizi* and *Phakopsora meibomiae*. Soybean rust caused by *Phakopsora pachyrhizi* is the most damaging disease affecting the yield of leguminous plants causing widespread damage to crops and depleting yield from 10 to 90% if not treated in time. Commonly known as Asian Soybean Rust (ASR), *Phakopsora pachyrhizi* infections must be detected early and treated early so as to prevent the geographic spread of the disease, which is airborne and causes severe loss of yield. The disease spreads through spores called urediniospores which are carried through the environs, resulting in wide spread damage. The disease earlier restricted to Asia and Australia has spread to Africa and in the past two decades, spread to South and North America. The first detection in the Americas was in 2001 in South America; from there it spread to North America where it was first detected in 2004.

*Phakopsora pachyrhizi* is known to infect over 30 legumes including commercially important edible beans as well as kudzu. The additional host crops serve as a reservoir for spores which can settle over the winter on the host crops and then spread in warmer weather. Early detection and treatment of *Phakopsora* is very essential to prevent the spread of disease and the loss of yield. Fungicides typically recommended for the treatment of this disease include Qo inhibitors (Quinone outside inhibitors), DM inhibitors (demethylation inhibitor), SDH Inhibitors (succinate dehydrogenase inhibitors). These fungicides when applied alone provided some control but, resistance was quickly observed, specifically in DM inhibitors (K Schmitz e al, Pest Management Science, Vol. 69, Issue 10 (2013)). Combination of Qo and DM inhibitors are also known in the art for the treatment of the disease, however, the treatment is not effective in controlling the disease and improving yields at the same time. Also, resistance to DM inhibitors effectively renders such combination compositions useless as the ASR strains can effectively overcome the effects of DM inhibitors. Venancio et. al (Poster #24, 2011 Field Crops Rust Symposium) taught the use of combination of stroilurins (Qo inhibitors) and triazoles (DM inhibitors) for the treatment of ASR, the control of the disease was found to be favorable; however, yield was significantly low, and some combinations showed lower disease control and significantly poor yield. Older studies have demonstrated the use of multi-site inhibitor fungicides such as chloronitriles and dithiocarbamate for the treatment of Soybean Rust; however, none of the multi-site inhibitor fungicides were successful in the control of the disease or the increase in yield.

The most important factor in Soybean Rust is the loss of foliage that results in the loss of nutrients and decrease in the overall yield of the crop. Numerous papers have been published that demonstrate moderate increase in yield with the application of fungicides. However, there is a need for a method of treatment that demonstrates improved yields along with preventive and/or curative capabilities in the treatment of Soybean Rust.

Compositions comprising the single actives used in the treatment of ASR have demonstrated very little control as compared to combinations, however, the cost and concentrations of such combination fungicides used in the treatment of ASR is significantly higher. There is therefore a need in the art for a method of treatment that provides excellent control over Asian Soybean Rust in host plants, as well as provides high yields, maintain nutrition and quality of the plants.

Hartman, G. L., Saadaoui, E. M, and Tschanz, A. T., Scientific eds. 1992, Annotated bibliography of soybean rust (*Phakopsora pachyrhizi* Sydow), A VRDC Library Bibliography Series 4-1, Tropical Vegetable Information Service. Taipei: Asian Vegetable Research and Development Center, recommended the use of triadimefon, thiabendazole, chlorothalonil and certain ethylenebis-dithiocarbamates for the control of soybean rust. The protection offered by triadimefon was inconsistent, in comparison to mancozeb, although it successfully prevented yield losses. However, triadimefon required frequent applications at 10-20 day intervals, starting from the flowering stage in order to retain its effectiveness. Thiabendazole was found to be less effective than certain ethylenebis-dithiocarbamates, and further was found effective only when used with oxycarboxin. Thiabendazole was also found to be phytotoxic. Chlorothalonii offered equal or worse rust control vis-a-vis the other fungicides recommended in this paper.

The use of ethylenebis-dithiocarbamates such as mancozeb, zineb or maneb alone has been found effective for the control of soybean rust when applied 7 to 21 days apart, provided the first application was made three weeks after planting and continued as late as till the flowering stage. Moreover, not all the studied showed yield increase due to the individual applications of ethylenebis-dithiocarbamates.

Oxycarboxin was found less effective than ethylenebis-dithiocarbamates, was found inconsistent in rust control and yield protection varied with the particular study. Oxycarboxin is also required to be applied when lesions first appear and then at 7-intervals for effective control, which is expensive and inconvenient.

Azoxystrobin is another fungicide, which has been recommended for soybean rust control. However, it is known in the art that a single late application of azoxystrobin does not control soybean rust or protect yield losses.

A recent survey by the present applicant found that a limited number of about 8-10 fungicides were approved to be used for the control of soybean rust, which are:
  (A) Conazole type fungicides such as myclobutanil, propiconazole, tetraconazole and tebuconazole;
  (B) Strobilurin type fungicides such as azoxystrobin and pyraclostrobin;
  (C) Combinations of conazole and strobilurin type fungicides such as propiconazole+trilfoxystrobin; and (D) Ethylenebis-dithiocarbamates such as mancozeb.

Thus, additional fungicides are needed for soybean rust control due to economic reasons as well as for resistance management strategies. However, the choice of fungicides for soybean is not straightforward.

Soybean is not usually treated with foliar fungicides. Therefore, the choice of a protective foliar fungicide leaves open the question of its application methods or the effect of the particular selected fungicide on the crop. The pathogen for soybean rust is usually found on the lower leaves of the plant where the lesion numbers increases as the inoculum builds up. As the plant begins to flower, this inoculum builds up increases and the infection moves up the plant as the lower leaves die off and drop. The crop needs protection from flowering stage to the pod fill stage, during which the plant canopy is very dense. The dense canopy is an effective barrier to penetration of fungicides applied over the top of the canopy. Therefore, foliar fungicides are not preferred during this stage of fungicidal control, or even the systemic fungicides that do not move down the plant system present a problem.

U.S. Pat. No. 8,044,084 discloses a method for controlling harmful fungi by applying a combination of a strobilurin fungicide with an ethylene modulator. It was found that the host plants are damaged to a lesser extent than after the treatment with a customary fungicide. Specifically, this patent teaches a combination of pyraciostrobin with prohexadione-Ca in weight ratio of from 20:1 to 0.05:1.

US 2011/0312493 teaches a method for controlling Asian soybean rust. The method comprises treating a glyphosate tolerant soybean plant propagation material with a fungicide selected from fiutriafoi, triticonazole, tebuconazole, ipconazole, epoxyconazole, orysastrobin, prothioconazole, fiuoxastrohin, azoxyscrobin, furametpyr, cyproconazole and subsequently with glyphosate.

US 2008/0153824 discloses for controlling rust infections in leguminous plants by using orysastrobin or a mixture of orysastrobin with azoles, acylaianines, amine derivatives, anilinopyximidines, dicarboximides, dithiocarbmates, heterocyclic compounds, phenylpyrroles, cinnamides and analogs thereof.

WO 2012/110464 discloses a method for controlling Asian soybean rust by applying a succinate dehydrogenase inhibitor fungicide.

There is a need in the art for a fungicidal method of control of soybean rust that takes into account the economics of fungicide application, the timing and number of sprays and lastly, the choice of the fungicide for an effective control. These issues present a considerable challenge to an agronomist.

Moreover, the single fungicide treatment regimen for Asian Soybean Rust (ASR) has many drawbacks. Azoxystrobin was one of the first of the Qo inhibitors to be used for the treatment of soybean rust individually and it provided good control. However, according to FRAC guidelines, Azoxystrobin should be used more as a preventive fungicide rather than a curative fungicide. The risk of resistance to Qo inhibitors is also very high. Another drawback is that even at the lowest labeled rate of use product, Qo inhibitor fungicide still costs the highest.

Alternatively, DM Inhibitors have shown good efficacy towards ASR, however, recent findings have suggested that *Phakopsora pachyrhizi* is capable of developing resistance to DM inhibitors.

Combinations of Qo inhibitors and DM inhibitors are currently registered in the Americas have demonstrated 40 to 60% control of ASR. However, the control efficacy mixtures of DM inhibitors with Qo inhibitors have reduced in the past seasons. Also, there is no great increase in yield and no decrease in the stress on the plant due to pest pressure.

Use of SDH inhibitors is also recommended for soybean rust control. However, single fungicides such as Boscalid offer only a moderate control of ASR.

Dithiocarbamates, and mancozeb in particular, was one of the first fungicides to be used for the treatment of ASR. Over the years many trials have been conducted on the use of Mancozeb alone for the treatment of ASR. However, the efficacy of mancozeb alone towards soybean rust control requires further research.

The present invention aims to overcome the problems in the prior art, namely, the need for a method of treatment that will not render *Phakopsora* resistant to actives, improve yield substantially and at reduced concentrations of actives, as well as reduced costs.

OBJECTS OF THE INVENTION

The present invention, described hereinafter, achieves at least one of the following objects of the invention.

It is an object of the present invention to provide a method to prevent and/or treat *Phakopsora pachyrhizi* and/or *Phakopsora meihomiae* infection in a host plant.

It is another object of the present invention to provide a method of treating Soybean Rust in a host plant that boosts the nutrient level in the plants and improves the quality of the plants.

It is another object of the present invention to provide a method of treating Soybean Rust in a host plant such that the quantities of fungicides used in the treatment is greatly reduced.

It is another object of the present invention to provide a method for treating soybean rust in a host plant wherein the fungicides used provides a synergistic control of soybean rust.

SUMMARY OF THE INVENTION

In an aspect, the present invention provides an improved method of treating soybean rust infection in a host leguminous plant, wherein the improvement comprises treating the plant at the locus of the infection with a dithiocarbamate fungicide, and concurrently, prior or subsequently to the dithiocarbamate fungicide, with at least another fungicide selected from a demethylation inhibitor, quinone outside inhibitor, succinate dehydrogenase inhibitor, quinone inside inhibitor or combinations thereof.

In another aspect, the present invention provides a fungicidal combination for treating soybean rust infection in a host leguminous plant, wherein the combination comprises a first dithiocarbamate fungicide, and at least second fungicide selected from a demethylation inhibitor, quinone outside inhibitor, succinate dehydrogenase inhibitor, quinone inside inhibitor or combinations thereof.

In another aspect, the present invention provides the use of a dithiocarbamate fungicide as a synergist to improve disease control in a host plant infected by soybean rust when applied subsequently, prior or concurrently to at least another fungicide selected from a demethylation inhibitor, quinone outside inhibitor, succinate dehydrogenase inhibitor, quinone inside inhibitor or combinations thereof.

DETAILED DESCRIPTION OF THE INVENTION

It has surprisingly been found that the use of a contact protective dithiocarbamate fungicide along with at least one systemic fungicide effectively penetrates the dense canopy barrier of the infected leguminous plant while simultaneously not allowing the rust pathogen to move up the plant foliage. Without wishing to be bound by theory, it is believed that the contact protective dithiocarbamate fungicide component of the combination effectively penetrates the dense plant foliage, while the systemic fungicide component effectively prevents the rust pathogen from infecting the remaining portion of the plant effectively reducing the susceptibility of the plant towards the infection. This synergistic complementation was not seen when either the foliar protective fungicide or the systemic fungicide were individually used in isolation, but was observed when the two fungicides were used in conjunction. This synergistic complementation between the contact preventive dithiocarbamate fungicide and a systemic fungicide for the treatment and control of *Phakopsora* species of fungicides was unexpected and surprising.

Thus, in an aspect, the present invention provides a method for treating soybean rust in a host leguminous plant, wherein the method comprises treating the plant at the locus of the infection with at least one multi-site contact fungicide; and concurrently, prior or subsequently to the multi-site contact fungicide, with at least one systemic fungicide.

The multi-site contact fungicides of the present invention inhibit fungal growth through multiple sites of action and have contact and preventive activity. In an embodiment, the multi-site contact fungicide may be selected from copper fungicides, sulfur fungicides, dithiocarbamate fungicides, phthalimide fungicides, chloronitrile fungicides, sulfamide fungicides, guanidine fungicides, triazines fungicides and quinone fungicides.

The copper fungicides of the present invention are inorganic compounds containing copper, typically in the copper (II) oxidation state and are preferably selected from copper oxychloride, copper sulfate, copper hydroxide and tribasic copper sulfate (Bordeaux mixture). The sulfur fungicides of the present invention are inorganic chemicals containing rings or chains of sulfur atoms and is preferably elemental sulfur. The dithiocarbamate fungicides of the present invention contain a dithiocarbamate molecular moiety and are selected from amobam, asomate, azithiram, carbamorph, cufraneb, cuprobam, disulfiram, ferbam, metam, nabam, tecoram, thiram, urbacide, ziram, dammet, etem, milneb, mancopper, mancozeb, maneb, metiram, polycarbamate, propineb and zineb. The phthalimide fungicides of the present invention contain a phthalimide molecular moiety and are selected from folpet, captan and captafol. The chloronitrile fungicide of the present invention comprises an aromatic ring substituted with chloro- and cyano-substituents and is preferably chlorothalonil. The sulfamide fungicides of the present invention are preferably selected from dichlofluanid and tolylfluanid. The guanidine fungicides of the present invention are preferably selected from dodine, guazantine and iminoctaadine. The triazine fungicide of the present invention is preferably anilazine. The quinone fungicide of the present invention is preferably dithianon.

In an embodiment, the multi-site contact fungicide of the present invention is a dithiocarbamate fungicide selected from amobam, asomate, azithiram, carbamorph, cufraneb, cuprobam, disulfiram, ferbam, metam, nabam, tecoram, thiram, urbacide, ziram, dammet, etem, milneb, mancopper, mancozeb, maneb, metiram, polycarbamate, propineb and zineb.

Thus, in this aspect, the present invention provides a method for treating soybean rust in a host leguminous plant, wherein the method comprises treating the plant at the locus of the infection with at least one dithiocarbamate fungicide selected from amobam, asomate, azithiram, carbamorph, cufraneb, cuprobam, disulfiram, ferbam, metam, nabam, tecoram, thiram, urbacide, ziram, dammet, etem, milneb, mancopper, mancozeb, maneb, metiram, polycarbamate, propineb and zineb; and concurrently, prior or subsequently to the dithiocarbamate fungicide, with at least one systemic fungicide.

In an embodiment, the dithiocarbamate fungicide is mancozeb.

In an embodiment, the multi-site contact fungicide is a combination of mancozeb and chlorothalonil.

Thus, in this embodiment, the present invention provides a method for treating soybean rust in a host leguminous plant, wherein the method comprises treating the plant at the locus of the infection with mancozeb; and concurrently, prior or subsequently to mancozeb, with at least one systemic fungicide.

The term contact fungicide as used herein for the dithiocarbamate fungicides denotes a fungicide that remains at the site where it is applied but does not travel within the plant. Typically, these fungicides do not show any post-infection activity.

In an embodiment, the contact dithiocarbamate fungicide may be applied repeatedly at the site of the infection at pre-determined time intervals.

The term "systemic fungicide" as used herein shall denote a fungicide that is absorbed into the plant tissue and possesses at least some amount of an after-infection activity. Preferably, the systemic fungicide of the present invention is capable of moving freely throughout the plant. However, the term "systemic fungicide" is intended herein to include the upwardly systemic fungicide as well as the locally systemic fungicide.

In an embodiment, the systemic fungicide is preferably a quinone outside inhibitor (Qol). In this embodiment, the quinone outside inhibitor is selected from an imidamlinone fungicide, an oxazolidinedione fungicide or a strobilurin fungicide.

Thus, in this embodiment, the present invention provides a method for treating soybean rust in a host leguminous plant, wherein the method comprises treating the plant at the locus of the infection with at least one dithiocarbamate fungicide selected from amobam, asomate, azithiram, carbamorph, cufraneb, cuprobam, disulfiram, ferbam, metam, nabam, tecoram, thiram, urbacide, ziram, dammet, etem, milneb, mancopper, mancozeb, maneb, metiram, polycarbamate, propineb and zineb, or combinations thereof with chlorothalonil; and concurrently, prior or subsequently to the dithiocarbamate fungicide, with at least one quinone outside inhibitor.

The Qol inhibitors useful in this embodiment of the present invention effect the inhibition of complex III: cytochrome bcl (ubiquinol oxidase) at Qo site i.e. cyt b gene.

In one embodiment, the imidamlinone fungicide is fenamidone.

In another embodiment, the oxazolidinedione fungicide is famoxadone.

In another embodiment, the strobilurin fungicide is selected from the group consisting of azoxystrobin, mandestrobin, coumoxystrobin, enoxastrobin, flufenoxystrobin, pyraoxystrobin, dimoxystrobin, enestrobin, fluoxastrobin, kresoxim-methyl, metominostrobin, orysastrobin, picoxystrobin, pyrametostrobin, triclopyricarb, fenaminstrobin, pyraclostrobin and trifloxystrobin.

In another embodiment, the systemic fungicide of the present invention is preferably a demethylation inhibitor (DMI).

Thus, in this embodiment, the present invention provides a method for treating soybean rust in a host leguminous plant, wherein the method comprises treating the plant at the locus of the infection with at least one dithiocarbamate fungicide selected from amobam, asomate, azithiram, carbamorph, cufraneb, cuprobam, disulfiram, ferbam, metam, nabam, tecoram, thiram, urbacide, ziram, dammet, etem, milneb, mancopper, mancozeb, maneb, metiram, polycarbamate, propineb and zineb or combinations thereof with chlorothalonil; and concurrently, prior or subsequently to the dithiocarbamate fungicide, with at least one demethylation inhibitor.

In this embodiment, the preferred DMI inhibitor is preferably a conazole fungicide selected from the group consisting of climbazole, clotrimazole, imazalil, oxpoconazole, prochloraz, prochloraz-manganese, triflumizole, azaconazole, bitertanol, bromuconazole, cyproconazole, diclobutrazol, difenoconazole, diniconazole, diniconazole-M, epoxiconazole, etaconazole, fenbuconazole, fluotrimazole, fluquinconazole, flusilazole, flutriafol, furconazole, furconazole-cis, hexaconazole, imibenconazole, ipconazole, metconazole, myclobutanil, pencoconazole, propiconazole, prothioconazole, quinconazole, simeconazole, tebuconazole, tetraconazole, triadimefon, triadimenol, triticonazole, uniconazole, perfurazoate and uniconazole-P.

In another embodiment, the preferred DMI inhibitor is preferably selected from triflumizole, triforine, pyridinitrile, pyrifenox, fenarimol, nuarimol and triarimol.

In another embodiment, the systemic fungicide of the present invention is a combination of at least one quinone outside inhibitor and at least demethylation inhibitor.

Thus, in this embodiment, the present invention provides a method for treating soybean rust in a host leguminous plant, wherein the method comprises treating the plant at the locus of the infection with at least one dithiocarbamate fungicide selected from amobam, asomate, azithiram, carbamorph, cufraneb, cuprobam, disulfiram, ferbam, metam, nabam, tecoram, thiram, urbacide, ziram, dammet, etem, milneb, mancopper, mancozeb, maneb, metiram, polycarbamate, propineb and zineb; and concurrently, prior or subsequently to the dithiocarbamate fungicide, with at least one quinone outside inhibitor and at least one demethylation inhibitor.

In an embodiment, the preferred quinone outside inhibitor is a strobilurin fungicide and the preferred demethylation inhibitor is a conazole fungicide. In this embodiment, the preferred dithiocarbamate is selected from the group consisting of thiram, ziram, mancozeb, maneb, metiram, propineb and zineb.

Therefore, in this embodiment, the present invention provides a method for treating soybean rust in a host leguminous plant, wherein the method comprises treating the plant at the locus of the infection with at least one dithiocarbamate fungicide selected from thiram, ziram, mancozeb, maneb, metiram, propineb and zineb or combinations thereof with chlorothalonil; and concurrently, prior or subsequently to the dithiocarbamate fungicide, with at least one strobilurin fungicide and at least one conazole fungicide.

In an embodiment, the preferred dithiocarbamate is mancozeb. In this embodiment, the preferred strobilurin fungicide is selected from trifloxystrobin, picoxystrobin, azoxystrobin or pyraclostrobin, while the preferred conazole fungicide is selected from prothioconazole, tebuconazole, cyproconazole, epoxiconazole, metconazole and tebuconazole.

Thus, in this embodiment, the present invention provides a method for treating soybean rust in a host leguminous plant, wherein the method comprises treating the plant at the locus of the infection with mancozeb or combinations thereof with chlorothalonil; and concurrently, prior or subsequently to mancozeb, with at least one strobilurin fungicide selected from trifloxystrobin, picoxystrobin, azoxystrobin or pyraclostrobin and at least one conazole fungicide selected from prothioconazole, tebuconazole, cyproconazole, epoxiconazole, metconazole and tebuconazole.

In one embodiment, the preferred strobilurin is trifloxystrobin and the preferred conazole is prothioconazole. Thus, in this embodiment, the present invention provides a method for treating soybean rust in a host leguminous plant, wherein the method comprises treating the plant at the locus of the infection with mancozeb; and concurrently, prior or subsequently to mancozeb, with trifloxystrobin and with prothioconazole.

In one embodiment, the preferred strobilurin is picoxystrobin and the preferred conazole is tebuconazole. Thus, in this embodiment, the present invention provides a method for treating soybean rust in a host leguminous plant, wherein the method comprises treating the plant at the locus of the infection with mancozeb; and concurrently, prior or subsequently to mancozeb, with picoxystrobin and with tebuconazole.

In one embodiment, the preferred strobilurin is picoxystrobin and the preferred conazole is cyproconazole. Thus, in this embodiment, the present invention provides a method for treating soybean rust in a host leguminous plant, wherein the method comprises treating the plant at the locus of the infection with mancozeb; and concurrently, prior or subsequently to mancozeb, with picoxystrobin and with cyproconazole.

In one embodiment, the preferred strobilurin is azoxystrobin and the preferred conazole is cyproconazole. Thus, in this embodiment, the present invention provides a method for treating soybean rust in a host leguminous plant, wherein the method comprises treating the plant at the locus of the infection with mancozeb; and concurrently, prior or subsequently to mancozeb, with azoxystrobin and with cyproconazole.

In one embodiment, the preferred strobilurin is pyraclostrobin and the preferred conazole is epoxiconazole. Thus, in this embodiment, the present invention provides a method for treating soybean rust in a host leguminous plant, wherein the method comprises treating the plant at the locus of the infection with mancozeb; and concurrently, prior or subsequently to mancozeb, with pyraclostrobin and with epoxiconazole.

In one embodiment, the preferred strobilurin is pyraclostrobin and the preferred conazole is tebuconazole. Thus, in this embodiment, the present invention provides a method for treating soybean rust in a host leguminous plant, wherein the method comprises treating the plant at the locus of the infection with mancozeb; and concurrently, prior or subsequently to mancozeb, with pyraclostrobin and with tebuconazole.

In one embodiment, the preferred strobilurin is pyraclostrobin and the preferred conazole is metconazole. Thus, in this embodiment, the present invention provides a method for treating soybean rust in a host leguminous plant, wherein the method comprises treating the plant at the locus of the infection with mancozeb; and concurrently, prior or subsequently to mancozeb, with pyraclostrobin and with metconazole.

In another embodiment, the preferred strobilurin is trifloxystrobin and the preferred conazole is selected from cyproconazole, propiconazole or tebuconazole. Thus, in this embodiment, the present invention provides a method for treating soybean rust in a host leguminous plant, wherein the method comprises treating the plant at the locus of the infection with mancozeb; and concurrently, prior or subsequently to mancozeb, with trifloxystrobin and with at least one compound selected from cyproconazole, propiconazole or tebuconazole.

In another embodiment, the systemic fungicide of the present invention is a quinone inside inhibitor. Preferably, the quinone inside inhibitor includes cyanoimidazole fungicides and sulfamoyltriazole fungicides.

In an embodiment, the quinone inside inhibitor is selected from cyazofamid and amisulbrom.

Thus, in this embodiment, the present invention provides a method for treating soybean rust in a host leguminous plant, wherein the method comprises treating the plant at the locus of the infection with at least one dithiocarbamate fungicide selected from amobam, asomate, azithiram, carbamorph, cufraneb, cuprobam, disulfiram, ferbam, metam, nabam, tecoram, thiram, urbacide, ziram, dammet, etem, milneb, mancopper, mancozeb, maneb, metiram, polycarbamate, propineb and zineb or combinations thereof with chlorothalonil; and concurrently, prior or subsequently to the dithiocarbamate fungicide, with at least one quinone inside inhibitor.

In another embodiment, the systemic fungicide of the present invention is a succinate dehydrogenase inhibitor fungicide (SDHI). Preferably, the succinate dehydrogenase inhibitor is selected from the group consisting of benodanil, flutolanil, mepronil, fluopyram, fenfuram, carboxin, oxycarboxin, thifluzamide, bixafen, fluxapyroxad, furametpyr, isopyrazam, penflufen, penthiopyrad, sedaxane and boscalid.

Thus, in this embodiment, the present invention provides a method for treating soybean rust in a host leguminous plant, wherein the method comprises treating the plant at the locus of the infection with at least one dithiocarbamate fungicide selected from amobam, asomate, azithiram, carbamorph, cufraneb, cuprobam, disulfiram, ferbam, metam, nabam, tecoram, thiram, urbacide, ziram, dammet, etem, milneb, mancopper, mancozeb, maneb, metiram, polycarbamate, propineb and zineb or combinations thereof with chlorothalonil; and concurrently, prior or subsequently to the dithiocarbamate fungicide, with at least one succinate dehydrogenase inhibitor.

It has been found that a combination of a multi-site contact fungicide, preferably a dithiocarbamate fungicide, along with a systemic fungicide selected from at least one Qo inhibitor (Quinone outside inhibitors), at least one Qi (quinone inside) inhibitor, at least one DM inhibitor (demethylation inhibitor) or at least one SDH Inhibitor (succinate dehydrogenase inhibitors) leads to an unexpected and surprisingly good control of Soybean Rust as compared to other fungicides reported in the art.

Surprisingly, it has been found that dithiocarbamates, preferably mancozeb or combinations thereof with chlorothalonil, acts as a synergist to improve disease control and plant health of a host legume plant infected with soybean rust when applied concurrently or subsequently to at least two fungicides selected from Qo inhibitors (Quinone outside inhibitors), DM inhibitors (demethylation inhibitor), SDH Inhibitors (succinate dehydrogenase inhibitors), Qi inhibitors (Quinone inside inhibitors) or combinations thereof. The present inventors believe that these combinations have never been hitherto reported in the art and many of their surprising properties never been envisaged. These combinations were found to possess surprisingly improved efficacy of enhanced disease control of Asian Soybean Rust caused by *Phakopsora pachyrhizi* and/or *Phakopsora meibomiae* infections. These combinations were also found to improve the quality of the plant by decreasing stress and improving nutrition levels, thereby increasing the yield of the plant that was infected with a fungicidal infection, especially with the soybean rust infection.

In an embodiment, these combinations were also found especially effective against corynespora, antbracnose, cercospora, leaf spot, rhizoctonia and sclerotinia families of fungi apart from their superior efficacy against *phakopsora* family of fungi.

Thus, in this aspect, the present invention provides a fungicidal combination comprising at least one multi-site contact fungicide, a first systemic fungicide and a second systemic fungicide.

In this aspect, the multi-site contact fungicide may be selected from copper fungicides, sulfur fungicides, dithiocarbamate fungicides, phthalimide fungicides, chloronitrile fungicides, sulfamide fungicides, guanidine fungicides, triazines fungicides and quinone fungicides.

The copper fungicides of this aspect are inorganic compounds containing copper, typically in the copper (II) oxidation state and are preferably selected from copper oxychloride, copper sulfate, copper hydroxide and tribasic copper sulfate (Bordeaux mixture).

The sulfur fungicides of this aspect are inorganic chemicals containing rings or chains of sulfur atoms and is preferably elemental sulfur.

The dithiocarbamate fungicides of this aspect contain a dithiocarbamate molecular moiety and are selected from amobam, asomate, azithiram, carbamorph, cufraneb, cuprobam, disulfiram, ferbam, metam, nabam, tecoram, thiram, urbacide, ziram, dammet, etem, milneb, mancopper, mancozeb, maneb, metiram, polycarbamate, propineb and zineb.

The phthalimide fungicides of this aspect contain a phthalimide molecular moiety and are selected from folpet, captan and captafol.

The chloronitrile fungicide of this aspect comprises an aromatic ring substituted with chloro- and cyano-substituents and is preferably chlorothalonil.

The sulfamide fungicides of this aspect are preferably selected from dichlofluanid and tolylfluanid.

The guanidine fungicides of this aspect are preferably selected from dodine, guazantine and iminoctaadine.

The triazine fungicide of this aspect is preferably anilazine.

The quinone fungicide of this aspect is preferably dithianon.

In an embodiment, the multi-site contact fungicide of this aspect is preferably selected from (a) a dithiocarbamate fungicide selected from amobam, asomate, azithiram, carbamorph, cufraneb, cuprobam, disulfiram, ferbam, metam, nabam, tecoram, thiram, urbacide, ziram, dammet, etem, milneb, mancopper, mancozeb, maneb, metiram, polycarbamate, propineb and zineb; and (b) a chloronitrile fungicide, which is chlorothalonil.

Thus, in this aspect, the present invention provides a fungicidal combination comprising:
(i) a multi-site contact fungicide selected from (a) a dithiocarbamate fungicide selected from amobam, asomate, azithiram, carbamorph, cufraneb, cuprobam, disulfiram, ferbam, metam, nabam, tecoram, thiram, urbacide, ziram, dammet, etem, milneb, mancopper, mancozeb, maneb, metiram, polycarbamate, propineb and zineb; or (b) a chloronitrile fungicide, which is chlorothalonil and combinations thereof;

(ii) a first systemic fungicide selected from a quinone outside inhibitor, a quinone inside inhibitor, demethylation inhibitor and succinate dehydrogenase inhibitor; and (iii) a second systemic fungicide selected from a quinone outside inhibitor, a quinone inside inhibitor, demethylation inhibitor and succinate dehydrogenase inhibitor.

In an embodiment, the first and second systemic fungicides are preferably different from each other.

In an embodiment, when the multi-site contact fungicide is a combination of mancozeb and chlorothalonil, the preferred systemic fungicide is at least one systemic fungicide selected from quinone outside inhibitor, quinone inside inhibitor, demethylation inhibitor or a succinate dehydrogenase inhibitor.

In a preferred embodiment, the first and second systemic fungicides are selected from different classes of systemic fungicides. For example:

(i) when the first systemic fungicide is a demethylation inhibitor, the second systemic fungicide is selected from a quinone outside inhibitor, a quinone inside inhibitor and succinate dehydrogenase inhibitor; or when (ii) the first systemic fungicide is a quinone outside inhibitor, the second systemic fungicide is selected from a quinone inside inhibitor, demethylation inhibitor and succinate dehydrogenase inhibitor; or when (iii) the first systemic fungicide is a quinone inside inhibitor, the second systemic fungicide is selected from a quinone outside inhibitor, a demethylation inhibitor and a succinate dehydrogenase inhibitor; or when (iv) the first systemic fungicide is a succinate dehydrogenase inhibitor, the second systemic fungicide is selected from a quinone outside inhibitor, a quinone inside inhibitor and a demethylation inhibitor.

Thus, in this aspect, the present invention provides a fungicidal combination comprising:

(i) a multi-site contact fungicide selected from (a) a dithiocarbamate fungicide selected from amobam, asomate, azithiram, carbamorph, cufraneb, cuprobam, disulfiram, ferbam, metam, nabam, tecoram, thiram, urbacide, ziram, dammet, etem, milneb, mancopper, mancozeb, maneb, metiram, polycarbamate, propineb and zineb; or (b) a chloronitrile fungicide, which is chlorothalonil or combination thereof;

(ii) a first systemic fungicide selected from a quinone outside inhibitor, a quinone inside inhibitor, demethylation inhibitor and succinate dehydrogenase inhibitor; and (iii) a second systemic fungicide selected from a quinone outside inhibitor, a quinone inside inhibitor, demethylation inhibitor and succinate dehydrogenase inhibitor;

such that (a) when the first systemic fungicide is a demethylation inhibitor, the second systemic fungicide is selected from a quinone outside inhibitor, a quinone inside inhibitor and succinate dehydrogenase inhibitor; or when (b) the first systemic fungicide is a quinone outside inhibitor, the second systemic fungicide is selected from a quinone inside inhibitor, demethylation inhibitor and succinate dehydrogenase inhibitor; or when (c) the first systemic fungicide is a quinone inside inhibitor, the second systemic fungicide is selected from a quinone outside inhibitor, a demethylation inhibitor and a succinate dehydrogenase inhibitor; or when (d) the first systemic fungicide is a succinate dehydrogenase inhibitor, the second systemic fungicide is selected from a quinone outside inhibitor, a quinone inside inhibitor and a demethylation inhibitor; or (e) when the multi-site contact fungicide is a combination of mancozeb and chlorothalonil, the systemic fungicide is at least one of a quinone outside inhibitor, a quinone inside inhibitor, a succinate dehydrogenase inhibitor and a demethylation inhibitor In a preferred embodiment, the preferred quinone outside inhibitor is a strobilurin fungicide and the preferred demethylation inhibitor is a conazole fungicide. In this embodiment, the preferred dithiocarbamate is selected from the group consisting of thiram, ziram, mancozeb, maneb, metiram, propineb and zineb.

Therefore, in this embodiment, the present invention provides a fungicidal combination comprising at least one multi-site contact fungicide selected from thiram, ziram, mancozeb, maneb, metiram, propineb, zineb and chlorothalonil or combinations thereof; at least one strobilurin fungicide and at least one conazole fungicide.

In an embodiment, the preferred dithiocarbamate is mancozeb. In this embodiment, the preferred strobilurin fungicide is selected from trifloxystrobin, picoxystrobin, azoxystrobin or pyraclostrobin, while the preferred conazole fungicide is selected from prothioconazole, tebuconazole, cyproconazole, epoxiconazole, metconazole and tebuconazole.

Thus, in this embodiment, the present invention provides a fungicidal combination comprising mancozeb or chlorothalonil or combinations thereof; at least one strobilurin fungicide selected from trifloxystrobin, picoxystrobin, azoxystrobin or pyraclostrobin and at least one conazole fungicide selected from prothioconazole, tebuconazole, cyproconazole, epoxiconazole, metconazole and tebuconazole.

In one embodiment, the preferred strobilurin is trifloxystrobin and the preferred conazole is prothioconazole. Thus, in this embodiment, the present invention provides a fungicidal combination comprising mancozeb or chlorothalonil; trifloxystrobin and prothioconazole.

In one embodiment, the preferred strobilurin is picoxystrobin and the preferred conazole is tebuconazole. Thus, in this embodiment, the present invention provides a fungicidal combination comprising mancozeb or chlorothalonil; picoxystrobin and tebuconazole.

In one embodiment, the preferred strobilurin is picoxystrobin and the preferred conazole is cyproconazole. Thus, in this embodiment, the present invention provides a fungicidal combination comprising mancozeb or chlorothalonil; picoxystrobin and cyproconazole.

In one embodiment, the preferred strobilurin is azoxystrobin and the preferred conazole is cyproconazole. Thus, in this embodiment, the present invention provides a fungicidal combination comprising mancozeb or chlorothalonil; azoxystrobin and cyproconazole.

In one embodiment, the preferred strobilurin is pyraclostrobin and the preferred conazole is epoxiconazole. Thus, in this embodiment, the present invention provides a fungicidal combination comprising mancozeb or chlorothalonil; pyraclostrobin and epoxiconazole.

In one embodiment, the preferred strobilurin is pyraclostrobin and the preferred conazole is tebuconazole. Thus, in this embodiment, the present invention provides a fungicidal combination comprising mancozeb or chlorothalonil; pyraclostrobin and tebuconazole.

In one embodiment, the preferred strobilurin is pyraclostrobin and the preferred conazole is metconazole. Thus, in this embodiment, the present invention provides a fungicidal combination comprising mancozeb or chlorothalonil; pyraclostrobin and metconazole.

In another embodiment, the preferred strobilurin is trifloxystrobin and the preferred conazole is selected from cyproconazole, propiconazole or tebuconazole. Thus, in this embodiment, the present invention provides a fungicidal combination comprising mancozeb or chlorothalonil; trifloxystrobin and at least one compound selected from cyproconazole, propiconazole or tebuconazole.

It was thus found that the addition of a dithiocarbamate fungicide to at least a demethylation inhibitor or a quinone outside inhibitor or a quinone inside inhibitor or a succinate dehydrogenase inhibitor or combinations thereof greatly increased the activity of the systemic fungicides over the expected disease control and expected yield.

In an embodiment, the application of the dithiocarbamate fungicide may be prior, subsequent or concurrent to the application of the systemic fungicide. When the systemic fungicide is applied subsequently to the dithiocarbamate fungicide, such sequential application of the systemic fungicide may be within 24 hours to 4 weeks of the application of the dithiocarbamate fungicide. In the case of concurrent application, the dithiocarbamate may be tank mixed with other actives or per-formulated mixtures may be conveniently used. The addition of mancozeb to existing combination products greatly increased the efficacy of the known combinations, thereby acting as a synergist, improving the rate of disease control and improving the overall health of the plant.

The amount of dithiocarbamate to be applied may range from 1 kg/ha to 2.5 kg/ha, preferred being 1.5 kg/ha to 2.0 kg ha.

In an embodiment, the dithiocarbamate may be applied in an effective amount so as to act as a synergist to the systemic fungicides of the present invention. However, the appropriate amounts of the fungicides used in the present invention, whether multi-site contact fungicides or systemic fungicides, is not particularly limiting and may be conveniently chosen by a skilled artisan.

The method of control of the present invention may be carried out by spraying the suggested tank mixes, or the individual fungicides may be formulated as a kit-of-parts containing various components that may be mixed as instructed prior to spraying.

In an embodiment, the fungicides or the combinations thereof contemplated according to the present invention may be pre-formulated and may be in the form of Water Dispersible Granules (WDG), Wettable Powders, Suspension Concentrates, Emulsifiable Concentrate, Suspoemulsions, Capsule Suspensions etc. However, the choice of any preferred formulation type is not particularly limiting.

Adjuvants and ancillary ingredients may be used to formulate such pre-formulated compositions and may employ wetters, adhesives, dispersants or surfactants and, if appropriate solvent or oil and other agriculturally acceptable additives.

In an embodiment, the present invention thus provides a composition comprising any of the fungicidal combinations such as herein described along with agriculturally acceptable excipients.

It is readily understood that the method of treatment of the present invention may be used on all host plants that are infected by both *Phakopsora pachyrhizi* and/or *Phakopsora meibomiae*. Such exemplary host plants may include soybean, Fenugreek, Kidney beans, Pinto beans, Fava or Broadbeans, Lima beans, Mung beans, Winged or Goa beans, Black-eyed Pea, Cowpea or Yard-long Bean, Green peas, Pigeon Pea, Swordbean, Urd or Black-gram etc.

As will be demonstrated in the examples, the addition of a multi-site contact fungicide to a systemic fungicide(s) for the treatment of ASR, greatly improved the disease control as well as improved yield. The lower the mixture performance in the rust control, the greater the additional benefit of the multi-site contact fungicide was seen.

The method of the present invention improves the existing disease control to an unexpectedly high degree and surprisingly improves the yield obtained. The method of the present invention also allows for greater resistance control and decreases the amount of the actives used.

These and other advantages of the invention may become more apparent from the examples set forth herein below. These examples are provided merely as illustrations of the invention and are not intended to be construed as a limitation thereof.

EXAMPLES

A study was conducted to determine the fungitoxicity of the multi-site contact fungicide, a dithiocarbamate fungicide mancozeb to *Phakopsora pachyrhizi* causal agent of Asian soybean rust (ASR) and the contribution of its incorporation to mixtures of strobilurin and triazole fungicides [demethylation inhibitor (DMI)+quinone outside inhibitor (Qol)]. Experiments were conducted in the field in nine locations where fungitoxicity of mancozeb to soybean rust was determined. Two doses were tested (1.5 and 2.0 kg/ha in various application numbers for mancozeb. The effect of mancozeb (1.5 kg/ha) incorporated to commercial mixtures was also tested. The tests were conducted on soybean cultivar Monsoy 9144 RR. A commercially available mancozeb 750 WDG (wettable granules) formulation was used for applying mancozeb. The combination mixtures were used as follows:

| S No. | Combination used | Dosage |
|---|---|---|
| A(1) | 200 g/L azoxystrobin + 80 g/L cyproconazole | 300 mL/Ha |
| A(2) | Mancozeb 750 WDG + 200 g/L azoxystrobin + 80 g/L cyproconazole | 1500 g/Ha + 300 mL/Ha |
| B(1) | 85 g/L pyraclostrobin + 62.5 g/L epoxiconazole | 500 mL/Ha |
| B(2) | Mancozeb 750 WDG + 85 g/L pyraclostrobin + 62.5 g/L epoxiconazole | 1500 g/Ha + 500 mL/Ha |
| C(1) | Cyproconazole 80 g/L + Picoxystrobin 200 g/L | 300 mL/Ha |
| C(2) | Mancozeb 750 WDG + Cyproconazole 80 g/L + Picoxystrobin 200 g/L | 1500 g/Ha + 300 mL/Ha |
| D(1) | Picoxystrobin 200 g/L + Tebuconazole 80 g/L | 300 mL/Ha |
| D(2) | Mancozeb 750 WDG + Picoxystrobin 200 g/L + Tebuconazole 80 g/L | 1500 g/Ha + 300 mL/Ha |

The percentage control of these experimental trials were noted and tabulated as hereunder:

| Fungicide applied | Assessment method | Percent control | Difference |
|---|---|---|---|
| A(1) | Percentage severity | 36.0 | — |
| A(2) | Percentage severity | 68.4 | +32.4% |
| A(1)-Replicate | Percentage severity | 40.0 | — |
| A(2)-Replicate | Percentage severity | 68.0 | +28.0% |
| B(1) | Percentage severity | 51.7 | — |
| B(2) | Percentage severity | 71.3 | +19.6% |

-continued

| Fungicide applied | Assessment method | Percent control | Difference |
|---|---|---|---|
| B(1)-Replicate | AUDPC-Area under disease progress curve | 55.6 | — |
| B(2)-Replicate | AUDPC | 71.7 | +20.7% |
| C(1) | AUDPC | 47.0 | — |
| C(2) | AUDPC | 74.0 | +27.0% |
| C(1)-Replicate | Percentage severity | 44.3 | — |
| C(2)-Replicate | Percentage severity | 54.4 | +11.1% |
| D(1) | AUDPC | 68.6 | — |
| D(2) | AUDPC | 90.2 | +21.7% |
| D(1)-Replicate | Percentage severity | 44.6 | — |
| D(2)-Replicate | Percentage severity | 52.0 | +7.4% |

It was thus found that the incorporation of mancozeb increased the rust control of the conventional strobilurin+ conazole fungicide treatment standard. It was further found that the lower the mixture performance in the rust control, the greater the additional benefit of mancozeb. It was thus concluded that the addition of a multi-site contact fungicide such as mancozeb acted as a synergist to the combination products registered for the treatment of Asian soybean rust. The addition of a dithiocarbamate increased disease control and improved yield of plants.

The instant invention is more specifically explained by above examples. However, it should be understood that the scope of the present invention is not limited by the examples in any manner. It will be appreciated by any person skilled in this art that the present invention includes aforesaid examples and further can be modified and altered within the technical scope of the present invention.

The invention claimed is:

1. A fungicidal combination, consisting of:

(i) mancozeb, (ii) prothioconazole, and (a) at least one succinate dehydrogenase inhibitor fungicide selected from the group consisting of benodanil, flutolanil, mepronil, fluopyram, fenfuram, carboxin, oxycarboxin, thifluzamide, bixafen, fluxapyroxad, furametpyr, isopyrazam, penflufen, penthiopyrad, sedaxane, and boscalid; or (b) at least one quinone outside inhibitor fungicides selected from the group consisting of fenamidone, famoxadone, and a strobilurin fungicide selected from the group consisting of azoxystrobin, mandestrobin, coumoxystrobin, enoxastrobin, flufenoxystrobin, pyraoxystrobin, dimoxystrobin, enestrobin, fluoxastrobin, kresoxim-methyl, metominostrobin, orysastrobin, picoxystrobin, pyrametostrobin, triclopyricarb, fenaminstrobin, pyraclostrobin and trifloxystrobin; or (c) at least one demethylation inhibitor fungicide selected from the group consisting of triflumizole, triforine, pyridinitrile, pyrifenox, fenarimol, nuarimol, triarimol, and a conazole fungicide selected from the group consisting of climbazole, clotrimazole, imazalil, oxpoconazole, prochloraz, prochloraz-manganese, triflumizole, azaconazole, bitertanol, bromuconazole, cyproconazole, diclobutrazol, difenoconazole, diniconazole, diniconazole-M, epoxiconazole, etaconazole, fenbuconazole, fluotrimazole, fluquinconazole, flusilazole, flutriafol, furconazole, imibenconazole, ipconazole, furconazole-cis, metconazole, hexaconazole, myclobutanil, pencoconazole, propiconazole, prothioconazole, quinconazole, simeconazole, tebuconazole, tetraconazole, triadimefon, triadimenol, triticonazole, uniconazole, perfurazoate, and uniconazole-P; and (iii) at least one agriculturally acceptable excipient.

2. The fungicidal combination according to claim 1, wherein (i) the strobilurin fungicide is selected from the group consisting of trifloxystrobin, picoxystrobin, azoxystrobin, and pyraclostrobin; and (ii) the conazole fungicide is selected from cyproconazole, epoxiconazole, metconazole, and tebuconazole.

3. The fungicidal combination according to claim 1, wherein the combination consists of mancozeb, prothioconazole, at least one succinate dehydrogenase inhibitor fungicide, and at least one agriculturally acceptable excipient.

4. The fungicidal combination according to claim 1, wherein the combination consists of mancozeb, prothioconazole, bixafen, and at least one agriculturally acceptable excipient.

5. The fungicidal combination according to claim 1, wherein the combination consists of mancozeb, prothioconazole, isopyrazam, and at least one agriculturally acceptable excipient.

6. The fungicidal combination according to claim 1, wherein the combination consists of mancozeb, prothioconazole boscalid, and at least one agriculturally acceptable excipient.

7. The fungicidal combination according to claim 1, wherein the combination consists of mancozeb, prothioconazole, azoxystrobin, and at least one agriculturally acceptable excipient.

8. The fungicidal combination according to claim 1, wherein the combination consists of mancozeb, prothioconazole, picoxystrobin, and at least one agriculturally acceptable excipient.

9. The fungicidal combination according to claim 1, wherein the combination consists of mancozeb, prothioconazole, pyraclostrobin, and at least one agriculturally acceptable excipient.

10. The fungicidal combination according to claim 1, wherein the combination consists of mancozeb, prothioconazole, trifloxystrobin, and at least one agriculturally acceptable excipient.

11. A method of treating soybean rust in a host leguminous plant, comprising:

applying to the plant at the locus of the infection a fungicidal combination according to claim 1.

12. A kit comprising a fungicidal combination consisting of:

(i) mancozeb, (ii) prothioconazole, and (a) at least one succinate dehydrogenase inhibitor fungicide selected from the group consisting of benodanil, flutolanil, mepronil, fluopyram, fenfuram, carboxin, oxycarboxin, thifluzamide, bixafen, fluxapyroxad, furametpyr, isopyrazam, penflufen, penthiopyrad, sedaxane, and boscalid; or (b) at least one quinone outside inhibitor fungicides selected from the group consisting of fenamidone, famoxadone, and a strobilurin fungicide selected from the group consisting of azoxystrobin, mandestrobin, coumoxystrobin, enoxastrobin, flufenoxystrobin, pyraoxystrobin, dimoxystrobin, enestrobin, fluoxastrobin, kresoxim-methyl, metominostrobin, orysastrobin, picoxystrobin, pyrametostrobin, triclopyricarb, fenaminstrobin, pyraclostrobin and trifloxystrobin; or (c) at least one demethylation inhibitor fungicide selected from the group consisting of triflumizole, triforine, pyridinitrile, pyrifenox, fenarimol, nuarimol, triarimol, and a conazole fungicide selected from the group consisting of climbazole, clotrimazole, imazalil, oxpoconazole, prochloraz, prochloraz-manganese, triflumizole, azaconazole, bitertanol, bromuconazole, cyproconazole, diclobutrazol, difenoconazole, diniconazole, diniconazole-M, epoxiconazole, etaconazole, fenbuconazole, fluotrimazole, fluquinconazole, flusilazole, flutriafol, furconazole, imibenconazole, ipconazole, furconazole-cis, metconazole, hexaconazole, myclobutanil, pencoconazole, propiconazole, prothioconazole, quinconazole, simeconazole, tebuconazole, tetraconazole, triadimefon, triadimenol, triticonazole, uniconazole, perfurazoate, and uniconazole-P; and (iii) at least one agriculturally acceptable excipient.

\* \* \* \* \*